US012402806B1

(12) United States Patent
McCue

(10) Patent No.: US 12,402,806 B1
(45) Date of Patent: Sep. 2, 2025

(54) WEARABLE SENSORS WITH HAPTIC FEEDBACK

(71) Applicant: Geoff McCue, Tonganoxie, KS (US)

(72) Inventor: Geoff McCue, Tonganoxie, KS (US)

( * ) Notice: Subject to any disclaimer, the term of this patent is extended or adjusted under 35 U.S.C. 154(b) by 0 days.

(21) Appl. No.: 19/071,809

(22) Filed: Mar. 6, 2025

(51) Int. Cl.
  *A61B 5/11* (2006.01)
  *A61B 5/00* (2006.01)
  *G08B 7/06* (2006.01)

(52) U.S. Cl.
  CPC .......... *A61B 5/1112* (2013.01); *A61B 5/1122* (2013.01); *A61B 5/6801* (2013.01); *G08B 7/06* (2013.01)

(58) Field of Classification Search
  CPC ... A61B 5/1112; A61B 5/1122; A61B 5/6801; G08B 7/06
  See application file for complete search history.

(56) References Cited

U.S. PATENT DOCUMENTS

| | | | | |
|---|---|---|---|---|
| 10,332,315 | B2* | 6/2019 | Samec | G16H 50/20 |
| 12,260,012 | B2* | 3/2025 | Ebert | G16H 50/30 |
| 2009/0306741 | A1* | 12/2009 | Hogle | A61N 1/36103 |
| | | | | 600/595 |
| 2017/0365101 | A1* | 12/2017 | Samec | G16H 20/70 |
| 2021/0342020 | A1* | 11/2021 | Jorasch | G06F 3/011 |
| 2025/0098965 | A1* | 3/2025 | Davies | A61B 5/01 |

OTHER PUBLICATIONS

Bruce et al. (Wearable Sensors to Monitor, Enable Feedback, and Measure Outcomes of Activity and Practice, (Year: 2018).*

* cited by examiner

*Primary Examiner* — Gertrude Arthur Jeanglaude
(74) *Attorney, Agent, or Firm* — Sam Pierce

(57) ABSTRACT

A wearable device integrating a network of interactive sensors is disclosed, wherein said sensors are configured to detect, monitor, and transmit real-time spatial position data to a central control unit. The central control unit comprises a processing module that computes the relative positioning and orientation of each sensor within a predefined reference frame, enabling continuous user movement tracking. Upon reaching a predefined spatial condition, the system generates a feedback signal, triggering a responsive sensory output via a haptic, auditory, or visual feedback mechanism. The device employs multiple positioning technologies, including inertial measurement units (IMUs), accelerometers, gyroscopes, magnetometers, radio frequency identification (RFID), Bluetooth Low Energy (BLE), ultra-wideband (UWB), and infrared tracking to ensure high-precision spatial awareness. The system is designed for applications in sports performance optimization, medical rehabilitation, virtual and augmented reality (VR/AR), occupational safety, and industrial hazard detection.

17 Claims, 4 Drawing Sheets

WEARABLE SENSORS WITH HAPTIC FEEDBACK

BACKGROUND OF THE INVENTION

Field of Invention

The present invention relates to the field of wearable technology, specifically to a wearable device embedded with interactive sensors that enable real-time location sensing and feedback mechanisms. More particularly, the invention focuses on enhancing user interaction, safety, and functionality by integrating sensor-based tracking and responsive feedback systems within a wearable garment or accessory. The invention finds applications in sports, healthcare, virtual and augmented reality (VR/AR), and occupational safety, providing users with improved spatial awareness and movement guidance.

BRIEF SUMMARY OF THE INVENTION

The present invention provides a wearable device embedded with a network of interactive sensors that monitor and transmit their real-time positions. These sensors communicate with a central controller, which processes the spatial data to determine the exact orientation and movement of the user. Upon reaching predefined positions, the device generates haptic feedback or other sensory responses, allowing for intuitive interaction and guidance.

The system employs various positioning technologies, such as inertial measurement units (IMUs), radio frequency identification (RFID), Bluetooth, and infrared tracking, to enhance precision. The device's adaptive feedback mechanisms enable real-time user engagement across multiple fields, including sports, healthcare, virtual reality (VR), and occupational safety. By providing continuous tracking and responsive feedback, the invention enhances movement accuracy, user awareness, and interactive experiences.

DETAILED DESCRIPTION

Figure 1:
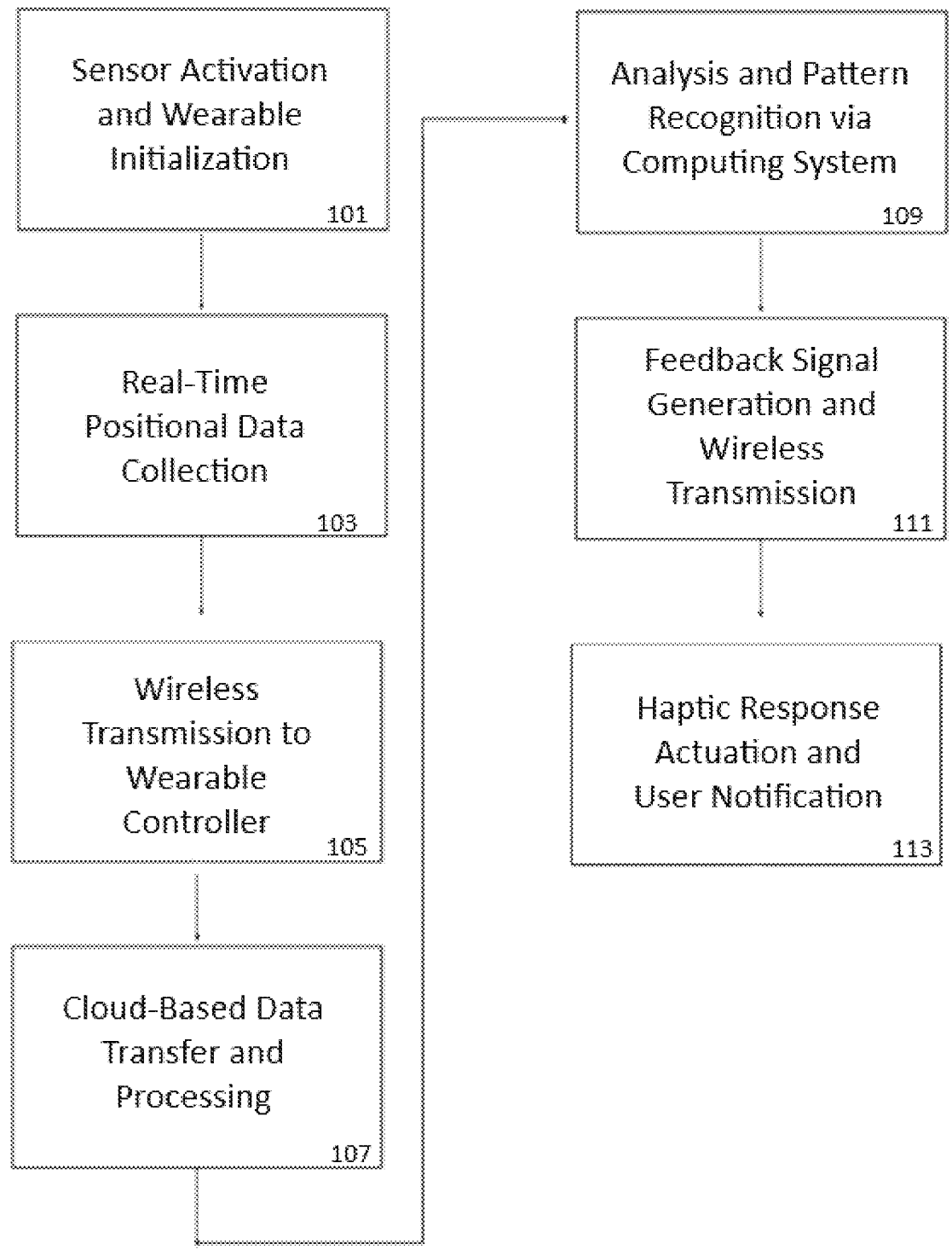
FIG. 1: The disclosed wearable device system initializes embedded sensors (Figure 1.101), collects real-time positional data (Figure 1.103), transmits sensor readings to the wearable controller (Figure 1.105), wirelessly transfers movement data to a cloud-based computational system (Figure 1.107), analyzes movement patterns using AI-driven models (Figure 1.109), generates an adaptive feedback signal (Figure 1.111), and actuates haptic response mechanisms to provide real-time corrective guidance to the user (Figure 1.113).

The present invention is directed to a wearable device incorporating an integrated system of interactive sensors, strategically positioned within a garment or accessory to facilitate precise real-time positional tracking and interactive feedback. More specifically, the wearable system comprises a plurality of sensor elements configured to detect and transmit their instantaneous geospatial positioning, kinematic state, and relative displacement data to a central control unit, which subsequently processes the data using computational methodologies designed to optimize tracking accuracy.

The control unit is programmed with advanced spatial localization algorithms that continuously analyze incoming sensor telemetry, enabling the determination of the precise orientation, movement patterns, and spatial relationships between individual sensor nodes relative to a predefined reference frame. The system is designed to provide real-time interactive feedback to the user through one or more haptic or sensory output mechanisms upon the fulfillment of predefined spatial conditions, thereby facilitating a seamless and highly responsive user experience.

The wearable device consists of a flexible, ergonomically designed structure incorporating sensor nodes that leverage a combination of inertial measurement units (IMUs), accelerometers, gyroscopes, magnetometers, ultra-wideband (UWB) modules, Bluetooth Low Energy (BLE) positioning, radio frequency identification (RFID) technology, and infrared tracking systems. Each sensor element is capable of continuously monitoring its absolute position and relative displacement from other sensor nodes, transmitting the acquired spatial data at predefined intervals to the central control unit for further processing.

The system's proprietary sensor fusion algorithms, based on Kalman filtering, extended Kalman filtering (EKF), or particle filtering techniques, dynamically integrate multi-sensor data, thereby mitigating the effects of drift, signal interference, and environmental perturbations that could otherwise compromise accuracy. The real-time computational architecture ensures that positional tracking is maintained with a high degree of precision, allowing the device to adaptively recalibrate and correct any detected deviations from expected movement trajectories.

Upon receiving the spatial data from individual sensor nodes, the control unit executes a multi-stage processing sequence to determine whether a specific sensor or group of sensors has reached a predefined position or orientation. The system achieves this by continuously referencing a stored database of predefined spatial configurations, which may correspond to expected movement patterns, postural alignments, or specific interaction states. The control unit's onboard processing system dynamically computes deviation metrics by comparing real-time sensor data against these predefined spatial reference points, allowing for immediate detection of positional accuracy, movement anomalies, or unintended variations in user motion. If the system determines that a designated movement criterion has been met, the control unit initiates a feedback response, transmitting an activation signal to the corresponding sensors, which in turn trigger one or more haptic actuators to deliver a responsive tactile output to the user.

The haptic feedback system integrated within the wearable device includes a plurality of vibrotactile motors, piezoelectric actuators, electrostatic stimulators, or neuromuscular stimulation interfaces, each of which is configured to deliver customized feedback responses based on real-time computational adjustments. The feedback intensity, duration, waveform profile, and activation timing of each response can be modulated dynamically based on multiple factors, including the degree of deviation from the predefined spatial reference point, the user's individual physiological characteristics, and environmental noise levels that may affect sensory perception.

In certain embodiments, the feedback mechanism may be augmented with supplementary response modalities, such as auditory alerts, visual cues, or augmented reality (AR) overlays, providing a multi-modal feedback system designed to optimize user engagement and response accuracy. The system may further incorporate biometric sensors capable of measuring physiological responses such as skin conductance, muscle activation levels, or heart rate variability, allowing for real-time adaptive modulation of feedback intensity based on the user's physiological state.

The device is designed to be applicable across multiple domains requiring high-precision real-time motion tracking and feedback-based interaction enhancement. In the field of sports and athletics, the device provides immediate kinematic assessment, allowing athletes to optimize movement patterns, posture, and technique in response to real-time feedback. The system can further assist in injury prevention by monitoring biomechanical alignment and detecting potentially hazardous deviations from optimal movement trajectories. In medical and rehabilitation applications, the wearable device serves as an intelligent physical therapy aid, ensuring that patients perform prescribed exercises with correct form and adherence to predefined rehabilitation protocols. The device's ability to generate real-time movement correction feedback makes it particularly well-suited for gait analysis, postural correction, and neuromuscular rehabilitation following injury or surgical intervention.

In the domain of virtual and augmented reality (VR/AR), the wearable device enhances immersion by providing precise body movement tracking and real-time synchronization between physical actions and digital representations. The system enables a seamless interaction between the user and virtual objects by translating real-world motion into high-fidelity spatial input, improving the accuracy and responsiveness of motion-capture systems.

Furthermore, in occupational safety and industrial applications, the system functions as an intelligent movement monitoring platform capable of alerting users to hazardous situations based on real-time spatial awareness. By integrating sensor-based tracking with predefined risk detection algorithms, the system can generate alerts when the user approaches a dangerous zone, deviates from safe operating postures, or fails to adhere to established safety protocols.

To facilitate interoperability with external systems, the wearable device is equipped with an advanced communication interface that supports multiple wireless and wired data transmission protocols, including Bluetooth, Wi-Fi, near-field communication (NFC), or proprietary radio frequency communication standards. The system enables bidirectional data exchange with external computing devices, allowing for the storage, analysis, and visualization of movement data over time. The collected data can be used to generate user-specific performance metrics, comparative movement analyses, and predictive modeling for future movement optimization. In some embodiments, the system may be integrated with cloud-based artificial intelligence (AI) platforms that utilize machine learning algorithms to continuously refine feedback models based on aggregated user data. This adaptive learning capability allows the system to improve its precision and responsiveness over time, ensuring that feedback remains optimally tuned to the user's evolving movement patterns and application-specific needs.

The present invention represents a significant advancement in the field of wearable technology by integrating real-time sensor-based location tracking with dynamically adjustable feedback mechanisms. Unlike conventional wearable systems that primarily focus on passive monitoring of physiological parameters, the disclosed invention actively enhances user interaction by providing immediate, precise, and adaptive feedback responses based on real-time spatial computations.

The system's ability to provide highly accurate movement tracking and correction makes it an invaluable tool across a wide range of professional and consumer applications, from athletic performance optimization to medical rehabilitation, virtual reality immersion, and industrial safety compliance. By offering a flexible, highly scalable architecture that can be adapted to various use cases, the invention ensures broad applicability while maintaining the highest standards of tracking precision, computational efficiency, and user-centered feedback design.

The disclosed system is designed to be modular and expandable, allowing for integration with future sensor technologies and feedback modalities as advancements in the field of wearable electronics and human-computer interaction continue to evolve. The ability to accommodate additional sensing modalities, including biometric feedback, force-sensitive resistors, or environmental sensors, ensures that the system remains adaptable to emerging requirements and industry standards. In addition, the device's ability to seamlessly integrate with cloud-based data processing platforms and AI-driven analytics tools positions it as a cutting-edge solution for motion analysis, interactive guidance, and real-time safety monitoring.

The present invention provides an innovative, highly technical, and legally enforceable wearable system that leverages real-time location sensing and interactive feedback mechanisms to enhance user engagement, motion precision, and situational awareness. By integrating advanced sensor technologies, computationally optimized tracking algorithms, and dynamically adjustable feedback systems, the invention establishes a new standard in wearable interaction, ensuring superior performance, versatility, and user adaptability across multiple industries and applications.

DETAILED DESCRIPTION OF FIGURES

Figure 1.101—Sensor Activation and Wearable Initialization

Upon placement on the user's body, the wearable device initializes by activating embedded interactive sensors. The device executes a self-diagnostic routine to ensure proper sensor functionality, power allocation, and connectivity with the wearable controller. Sensors—including inertial measurement units (IMUs), accelerometers, gyroscopes, and RFID/Bluetooth/UWB positioning elements—begin continuously capturing spatial orientation, motion vector data, and relative positioning metrics. The initialization phase also involves establishing a secure connection with the wearable controller, which serves as the intermediary processing unit for subsequent operations.

Figure 1.103—Real-Time Positional Data Collection

Once the wearable device is active, its integrated sensors continuously monitor the user's movement, generating high-resolution spatial data. The sensors track variables such as absolute position, velocity, acceleration, and angular displacement, while multi-sensor fusion techniques refine accuracy by mitigating drift or signal interference. This data is dynamically adjusted based on user movement patterns and environmental interactions, ensuring real-time responsiveness.

Figure 1.105—Wireless Transmission to Wearable Controller

Captured sensor data is transmitted via a low-latency communication protocol—such as Bluetooth Low Energy (BLE), ultra-wideband (UWB), or RFID—to the wearable controller. The wearable controller acts as a real-time computational gateway, aggregating, filtering, and preprocessing incoming sensor data. The controller may apply preliminary movement recognition algorithms or compression techniques to optimize the transmission of data packets while reducing power consumption.

Figure 1.107—Cloud-Based Data Transfer and Processing

Following preprocessing, the wearable controller initiates a secure wireless data transfer to a cloud-based computational infrastructure. The data is encrypted and transmitted over Wi-Fi or cellular networks to remote servers, where it is indexed and prepared for advanced analytics. The cloud system facilitates large-scale data storage, ensuring that historical movement records, real-time positional updates, and predictive analytics can be accessed and processed efficiently.

Figure 1.109—Analysis and Pattern Recognition Via Computing System

The received data undergoes high-speed analysis through cloud-hosted machine learning algorithms and artificial intelligence (AI)-based predictive models. These computational processes detect movement deviations, recognize predefined motion patterns, and assess user compliance with expected movement trajectories. If a discrepancy is identified—such as improper posture, excessive deviation, or suboptimal movement efficiency—the system determines an appropriate corrective action and prepares a corresponding feedback response.

Figure 1.111—Feedback Signal Generation and Wireless Transmission

Based on the computed analysis, the cloud-based system formulates a feedback response, which is then relayed back to the wearable controller via a secure wireless channel. This response signal encodes parameters for haptic actuation, specifying vibration intensity, waveform modulation, and duration based on the user's detected movement deviations. The controller then deciphers the response and prepares to actuate the appropriate haptic mechanisms embedded within the wearable device.

Figure 1.113—Haptic Response Actuation and User Notification

Upon receiving the corrective feedback signal, the wearable device activates its embedded haptic actuators—such as vibrotactile motors, electrostatic stimulators, or neuromuscular stimulators—to provide real-time user notification. The intensity and frequency of the haptic response are modulated based on the degree of movement deviation or predefined feedback thresholds. Simultaneously, an optional secondary alert—such as a smartphone notification or auditory signal—may be triggered to provide supplementary guidance or detailed corrective instructions.

Figure 2:
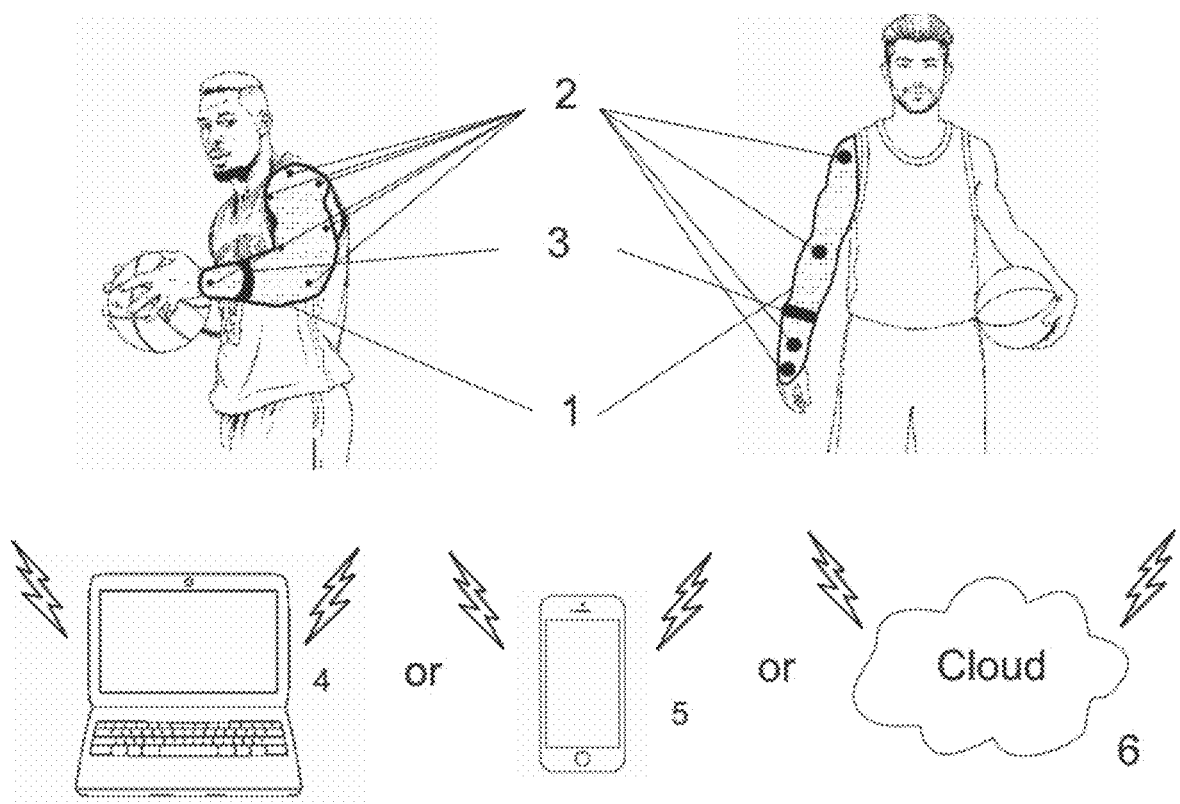
FIG. 2 illustrates the wearable sensor system on an athlete, showing the wearable (1), sensors (2), wearable controller (3), master controller in the form of a computer (4), smartphone (5), and cloud infrastructure (6), all working together to enable real-time movement tracking, data transmission, and feedback processing.

FIG. 2—Wearable Sensor System on an Athlete

FIG. 2 provides a comprehensive illustration of the wearable sensor system as applied to an athlete, detailing the integration and interaction between the device's core components. The wearable (1) is configured as a flexible, form-fitting garment embedded with sensors (2) that continuously monitor the athlete's biomechanical movements, capturing real-time data such as acceleration, angular velocity, and positional shifts. These sensors communicate wirelessly with a wearable controller (3), which serves as an intermediary processing unit responsible for pre-filtering sensor input, executing preliminary data computations, and optimizing transmission efficiency. The wearable controller transmits structured movement data to a master controller (4), which may be implemented as a high-performance computing system equipped with advanced analytical software for motion tracking and feedback optimization. Additionally, the system interfaces with a smartphone (5), allowing users to access real-time movement statistics, receive performance feedback, and customize device parameters. Data synchronization is further facilitated through cloud infrastructure (6), enabling remote data storage, AI-driven motion analysis, and historical performance tracking. The illustrated configuration highlights the system's modular and scalable architecture, ensuring seamless integration across multiple devices and computing platforms.

Figure 3:
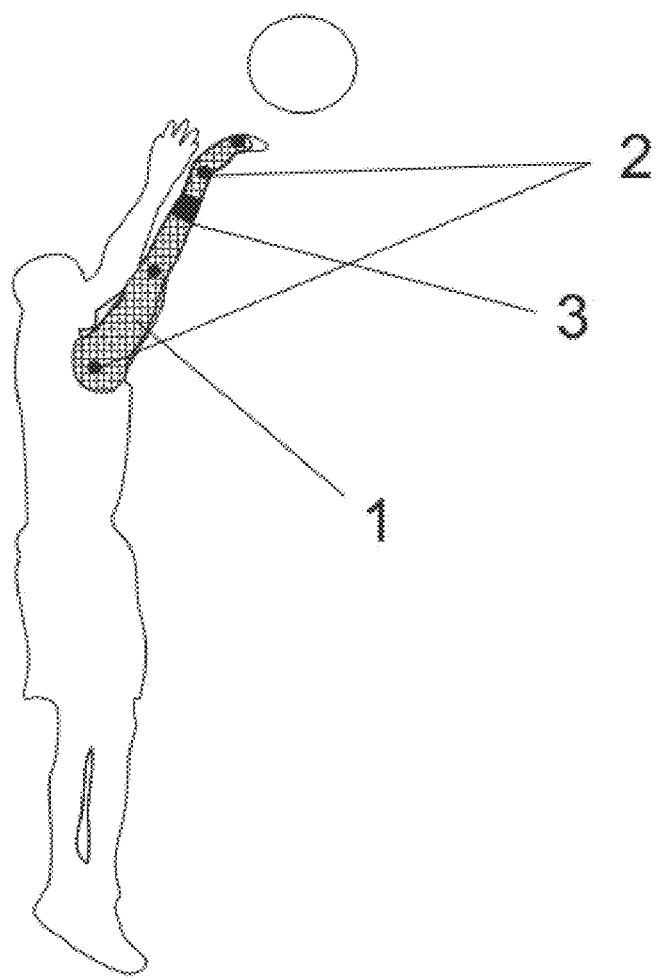
FIG. 3 depicts the wearable sensor system in operation during a jump shot, where the wearable (1), sensors (2), and wearable controller (3) capture body mechanics, track motion trajectories, and transmit movement data for performance analysis and feedback generation.

FIG. 3—Wearable Sensor System During a Jump Shot

FIG. 3 depicts the wearable sensor system actively monitoring an athlete executing a jump shot, demonstrating its application in analyzing vertical motion, body alignment, and shooting mechanics. The wearable (1) conforms to the athlete's body, with strategically positioned sensors (2) continuously capturing joint angles, force distribution, and upper-limb coordination during the preparatory, execution, and follow-through phases of the shot. These sensors transmit real-time movement data to the wearable controller (3), which processes motion kinematics, identifying deviations from optimal shooting form. The system detects critical biomechanical parameters such as knee flexion, elbow positioning, and wrist snap velocity, providing real-time analytical feedback to refine shooting technique. The wearable controller transmits motion telemetry to an external computing system for AI-driven analysis, allowing users to receive precision feedback via a connected smartphone or cloud-based platform. The figure emphasizes how the system facilitates performance optimization and biomechanical correction through real-time movement tracking and dynamic feedback generation.

Figure 4:
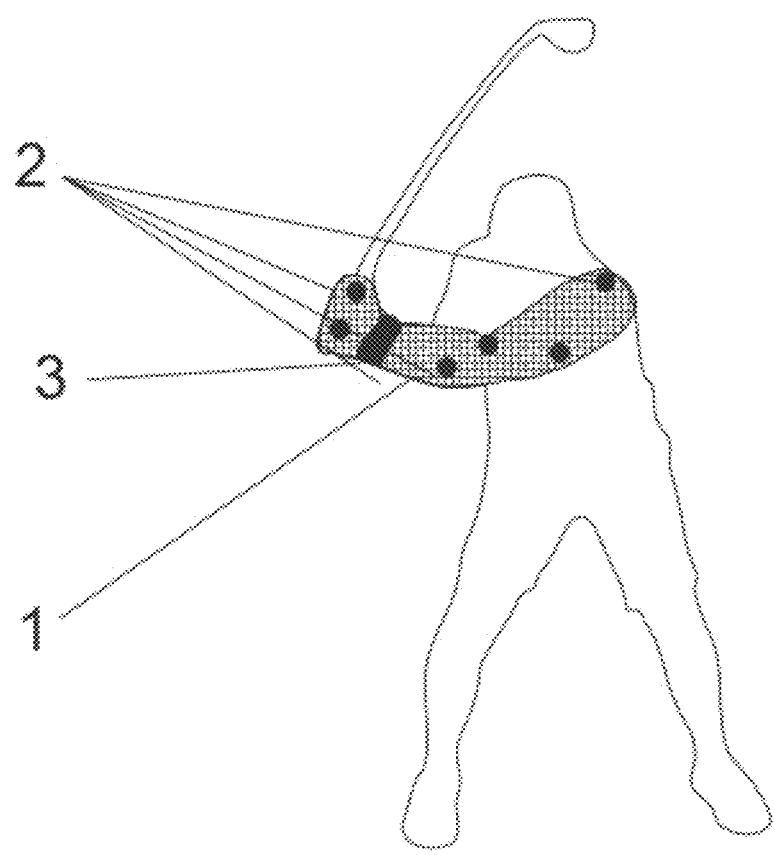
FIG. 4 demonstrates the wearable sensor system monitoring a golf swing, where the wearable (1), sensors (2), and wearable controller (3) detect rotational movement, assess posture stability, and provide real-time corrective feedback to refine swing mechanics.

FIG. 4—Wearable Sensor System During a Golf Swing

FIG. 4 illustrates the wearable sensor system applied to a golf swing, highlighting its functionality in tracking rotational motion, stance stability, and swing mechanics. The wearable (1) is fitted with high-precision sensors (2), strategically positioned to capture full-body kinematics, including hip rotation, shoulder movement, and club path alignment. These sensors interface with the wearable controller (3), which collects and processes dynamic swing data, identifying critical performance metrics such as backswing angle, downswing velocity, and follow-through stability. The system employs advanced motion pattern recognition algorithms to detect inconsistencies in the swing path, weight distribution anomalies, and timing inefficiencies. The wearable controller transmits this data to an external computing platform, allowing AI-based motion analysis to generate personalized recommendations for swing refinement. The figure showcases the system's ability to provide precise real-time feedback, enabling golfers to fine-tune mechanics, improve shot accuracy, and enhance overall performance consistency.

What is claimed is:

1. A wearable device, comprising:
   a. a plurality of interactive sensors embedded within a wearable structure, each sensor configured to monitor its real-time spatial position and transmit corresponding location data;
   b. a central control unit operatively coupled to said plurality of interactive sensors, the central control unit comprising a processing module configured to:
      i. receive real-time spatial position data from said plurality of interactive sensors,
      ii. compute the relative positioning and orientation of each sensor within a predefined spatial reference frame, and
      iii. generate a real-time haptic feedback signal with real-time adaptive modulation of feedback intensity based on the user's physiological state when one or more of said sensors achieve a predefined spatial condition; and
   c. a feedback mechanism operatively coupled to said plurality of interactive sensors, wherein said feedback mechanism is configured to provide a sensory output upon receipt of said feedback signal, wherein feedback intensity, duration, waveform profile, and activation timing of each response are modulated in real-time based on the degree of deviation from the predefined spatial reference point.

2. The wearable device of claim 1, wherein said plurality of interactive sensors comprises at least one of: inertial measurement units (IMUs), accelerometers, gyroscopes, magnetometers, radio frequency identification (RFID) modules, Bluetooth Low Energy (BLE) positioning modules, ultra-wideband (UWB) transceivers, and infrared tracking elements.

3. The wearable device of claim 1, wherein said processing module further comprises a sensor fusion algorithm configured to integrate multi-sensor data using at least one of Kalman filtering, extended Kalman filtering (EKF), or particle filtering techniques to improve spatial tracking accuracy.

4. The wearable device of claim 1, wherein said central control unit is further configured to compare real-time sensor position data against stored reference spatial configurations to determine movement deviations, compliance with predefined movement patterns, or corrective guidance parameters.

5. The wearable device of claim 1, wherein said feedback mechanism comprises at least one of: vibrotactile actuators, piezoelectric stimulators, electrostatic feedback elements, neuromuscular stimulation devices, auditory output devices, or visual display indicators.

6. The wearable device of claim 1, wherein said feedback mechanism is further configured to modulate the intensity, duration, waveform profile, or activation frequency of said sensory output based on at least one of: user-defined parameters, environmental noise interference, or real-time physiological sensor input.

7. The wearable device of claim 1, further comprising a communication module configured to facilitate wireless data exchange between the central control unit and an external computing device using at least one of: Wi-Fi, Bluetooth, near-field communication (NFC), or a proprietary radio frequency protocol.

8. The wearable device of claim 1, wherein said processing module is further configured to execute a machine-learning-based adaptive feedback algorithm that continuously refines feedback response patterns based on historical user interaction data.

9. The wearable device of claim 1, wherein said central control unit further comprises a data storage module configured to store sensor position logs, movement trajectory records, or user interaction histories for subsequent analysis.

10. The wearable device of claim 1, wherein said wearable structure is configured as at least one of: a garment, sleeve, glove, armband, leg wrap, exoskeletal framework, or a combination thereof.

11. The wearable device of claim 1, wherein said system is configured to operate in at least one of the following applications: sports performance optimization, medical rehabilitation, virtual and augmented reality (VR/AR) movement tracking, occupational safety monitoring, or industrial hazard detection.

12. The wearable device of claim 1, wherein the wearable device conforms to the athlete's body with strategically positioned sensors continuously capturing joint angles, force distribution, and upper-limb coordination during the preparatory, execution, and follow-through phases of a movement and the strategically positioned sensors transmit real-time movement data to the wearable controller which processes motion kinematics to identify deviations from optimal movement form and detect one or more biomechanical parameters selected from the group comprising flexion, positioning, and velocity.

13. The wearable device of claim 1, wherein the wearable device captures full-body kinematics comprising rotation, movement, and alignment and interfaces with the wearable controller to collect and process dynamic swing data to identify critical performance metrics comprising one or more of angle, velocity, and follow-through stability and detect inconsistencies in the movement, weight distribution anomalies, and timing inefficiencies.

14. A method for real-time spatial tracking and interactive feedback in a wearable device, the method comprising:
   a. receiving real-time spatial position data from a plurality of interactive sensors embedded within a wearable structure;
   b. processing the received position data using a central control unit configured to compute the relative position, orientation, and movement trajectory of each sensor within a predefined spatial reference frame;
   c. \comparing the computed movement trajectory against stored reference spatial configurations to determine deviations, target position achievement, or corrective movement guidance parameters;
   d. generating a feedback signal upon detection of a predefined spatial condition, wherein the feedback signal is a real-time haptic feedback signal with real-time adaptive modulation of feedback intensity based on the user's physiological state; and
   e. actuating a feedback mechanism to provide a sensory output corresponding to the feedback signal, wherein feedback intensity, duration, waveform profile, and activation timing of each response are modulated in real-time based on the degree of deviation from the predefined spatial reference point.

15. The method of claim 14, further comprising dynamically adjusting the feedback mechanism's intensity, duration, waveform profile, or frequency in response to at least one of: user-defined sensitivity preferences, movement deviation magnitude, real-time environmental conditions, or biometric sensor inputs.

16. The method of claim 14, further comprising transmitting spatial position data to an external computing device for storage, analysis, and predictive modeling of user movement patterns.

17. The method of claim 14, further comprising applying a machine-learning algorithm to continuously refine and personalize feedback response logic based on accumulated historical movement data.

* * * * *